(12) United States Patent
Coleman et al.

(10) Patent No.: US 10,933,134 B2
(45) Date of Patent: Mar. 2, 2021

(54) COMBINATION THERAPIES FOR TREATMENT OF CANCER

(71) Applicants: Memorial Sloan Kettering Cancer Center, New York, NY (US); Yeda Research and Development Co. Ltd., at the Weizmann Institute of Science, Rehovot (IL)

(72) Inventors: Jonathan Coleman, Scarsdale, NY (US); Philip A. Watson, New York, NY (US); Kwanghee Kim, New York, NY (US); Avigdor Scherz, Rehovot (IL)

(73) Assignees: Memorial Sloan Kettering Cancer Center, New York, NY (US); Yeda Research and Development Co. Ltd., at the Weizmann Institute of Science, Rehovot (IL)

( * ) Notice: Subject to any disclaimer, the term of this patent is extended or adjusted under 35 U.S.C. 154(b) by 0 days.

(21) Appl. No.: 15/924,039

(22) Filed: Mar. 16, 2018

(65) Prior Publication Data
US 2018/0296675 A1 Oct. 18, 2018

Related U.S. Application Data

(60) Provisional application No. 62/472,126, filed on Mar. 16, 2017.

(51) Int. Cl.
| | |
|---|---|
| *A61K 41/00* | (2020.01) |
| *A61P 35/00* | (2006.01) |
| *A61K 31/4166* | (2006.01) |
| *A61K 38/08* | (2019.01) |
| *A61K 47/64* | (2017.01) |
| *A61N 5/06* | (2006.01) |

(52) U.S. Cl.
CPC ...... *A61K 41/0071* (2013.01); *A61K 31/4166* (2013.01); *A61K 38/08* (2013.01); *A61K 47/64* (2017.08); *A61P 35/00* (2018.01); *A61N 5/062* (2013.01)

(58) Field of Classification Search
None
See application file for complete search history.

(56) References Cited

U.S. PATENT DOCUMENTS

| | | |
|---|---|---|
| 7,947,672 B2 | 5/2011 | Scherz et al. |
| 8,461,142 B2 | 6/2013 | Scherz et al. |
| 8,673,270 B2 | 3/2014 | Eren et al. |
| 8,815,213 B2 | 8/2014 | Scherz et al. |
| 2010/0305042 A1* | 12/2010 | Olesen ............... A61K 9/0019 514/19.5 |
| 2012/0294801 A1 | 11/2012 | Scherz et al. |

FOREIGN PATENT DOCUMENTS

| | | |
|---|---|---|
| WO | 2000/033833 A1 | 6/2000 |
| WO | 2004/045492 A2 | 6/2004 |
| WO | 2008/023378 A1 | 2/2008 |
| WO | 2009/107139 A1 | 9/2009 |
| WO | 2010/046900 A2 | 4/2010 |

OTHER PUBLICATIONS

Ashur I. et al., "Photocatalytic generation of oxygen radicals by the water-soluble bacteriochlorophyll derivative WST11, noncovalently bound to serum albumin," J Phys Chem A 113:8027-37 (2009).
Azzouzi A-R. et al., "TOOKAD® Soluble focal therapy: pooled analysis of three phase II studies assessing the minimally invasive ablation of localized prostate cancer," World J Urol 33:945-53 (2015).
Azzouzi A-R. et al., "Padeliporfin vascular-targeted photodynamic therapy versus active surveillance in men with low-risk prostate cancer (CLIN1001 PCM301): an open-label, phase randomised controlled trial," Lancet Oncol 13:181-91 (2017).
Borle F. et al., "Selectivity of the photosensitiser Tookad for photodynamic therapy evaluated in the Syrian golden hamster cheek pouch tumour model," Br J Cancer 89:2320-26 (2003).
Brandis A. et al., "Novel water-soluble bacteriochlorophyll derivatives for vascular-targeted photodynamic therapy: synthesis, solubility, phototoxicity and the effect of serum proteins," Photochem Photobiol. 81:983-93 (2005).
Broekgaarden M. et al., "Tumor cell survival pathways activated by photodynamic therapy: a molecular basis for pharmacological inhibition strategies," Cancer Metastasis Rev 34:643-90 (2015).
Broqua P. et al., "Pharmacological profile of a new, potent, and long-acting gonadotropin-releasing hormone antagonist: degarelix," J Pharmacol Exp Ther. 301:95-102 (2002).
Cathelineau X. et al., "Focal Therapy for Prostate Cancer: Pending Questions," Curr Urol Rep. 17:86 (2016).
Chen CD. et al., "Molecular determinants of resistance to antiandrogen therapy," Nat Med. 10:33-39 (2004).
Klotz L. et al., "The efficacy and safety of degarelix: a 12-month, comparative, randomized, open-label, parallel-group phase III study in patients with prostate cancer," BJU Int. 102:1531-8 (2008).
Lebdai S. et al., "Vascular Targeted Photodynamic Therapy with Padeliporfin for Low Risk Prostate Cancer Treatment: Midterm Oncologic Outcomes," J Urol 198(2):335-344 (2017).
Mitrunen K. et al., "Dual-label one-step immunoassay for simultaneous measurement of free and total prostate-specific antigen concentrations and ratios in serum," Clin Chem 41:1115-20 (1995).
Pettersson K. et al., "Free and complexed prostate-specific antigen (PSA): in vitro stability, epitope map, and development of immunofluorometric assays for specific and sensitive detection of free PSA and PSA-alpha 1-antichymotrypsin complex," Clin Chem. 41:1480-88 (1995).
Preise D. et al., "Systemic antitumor protection by vascular-targeted photodynamic therapy involves cellular and humoral immunity," Cancer Immunol Immunother. 58:71-84 (2009).

(Continued)

*Primary Examiner* — Thomas S Heard
(74) *Attorney, Agent, or Firm* — Dechert LLP

(57) ABSTRACT

A method for treatment of prostate cancer or benign prostate hyperplasia by combination therapy comprising administering to a patient an androgen-deprivation therapy agent and a bacteriochlorophyll derivative followed by photodynamic therapy (PDT) or vascular-targeted photodynamic therapy (VTP).

18 Claims, 8 Drawing Sheets
(8 of 8 Drawing Sheet(s) Filed in Color)

(56) References Cited

OTHER PUBLICATIONS

Subramanian A. et al., "Gene set enrichment analysis: a knowledge-based approach for interpreting genomewide expression profiles," Proc Natl Acad Sci USA. 102:15545-50 (2005).

Ulmert D. et al., I"maging androgen receptor signaling with a radiotracer targeting free prostate-specific antigen," Cancer Discov. 2:320-27 (2012).

Agemy et al., 2016 "Enhancing antitumor immunity by photodynamic therapy with gemcitabine in metastatic 4T1 breast tumor," Ann Oncol 27(Suppl 9):124-125 401P (2 pages).

Obradovic et al., 2020 "T-Cell Infiltration and Adaptive Treg Resistance in Response to Androgen Deprivation With or Without Vaccination in Localized Prostate Cancer," Clin Cancer Res doi: 10.1158/1078-0432.CCR-19-3372 (12 pages).

Preise et al., 2011 "Antitumor immunity promoted by vascular occluding therapy: lessons from vascular-targeted photodynamic therapy (VTP)," Photochem Photobiol Sci 10:681-688.

Preise et al., 2009, "Systemic antitumor protection by vascular-targeted photodynamic therapy involves cellular and humoral immunity," Cancer Immunol. Immunother 58:71-84.

Shen et al., 2018 "Combining Intra-Tumoral Treg Depletion with Androgen Deprivation Therapy (ADT): Pre-Clinical Activity in the Myc-CaP Model," Prostate Cancer Prostatic Dis 21(1):113-125.

Bohmer et al., 2016 "Radiotherapy and Hormone Treatment in Prostate Cancer," Dtsch Arztebl Int 113(14): 235-41.

Jones et al., 2011 "Radiotherapy and Short-Term Androgen Deprivation for Localized Prostate Cancer," N Engl J Med 365(2):107-18.

Kalina et al., 2017 "Immune Modulation by Androgen Deprivation and Radiation Therapy: Implications for Prostate Cancer Immunotherapy," Cancers 9, 13 pp. 1-25.

Kim et al., 2016 "Abstract 3389: Androgen deprivation therapy potentiates the efficacy of vascular targeted photodynamic therapy of prostate cancer xenografts," Cancer Res (76) (14 Suppl) 3389 (2 pages).

\* cited by examiner

COMBINATION THERAPIES FOR TREATMENT OF CANCER

RELATED APPLICATION

This application claims priority to and the benefit of provisional application U.S. 62/472,126 filed Mar. 16, 2017, which is incorporated by reference herein in its entirety as if fully disclosed therein.

FIELD OF THE INVENTION

The present invention relates to treatment of cancer and to combination therapies therefore. In particular, the invention relates to treatment of prostate cancer or benign prostate hyperplasia by combination therapy.
DEFINITIONS AND ABBREVIATIONS: ADT: androgen deprivation therapy; AR: androgen receptor; Bchl: bacteriochlorophyll: Bchl-D: bacteriochlorophyll derivative; BPH: benign prostate hyperplasia; GSEA: Gene Set Enrichment Analysis; LNCaP-AR: a prostate cancer cell line that overexpresses the androgen receptor; Padeliporfin: generic name for TOOKAD; PCa: Prostate cancer; PDT: photodynamic therapy; PSA: prostate-specific antigen; ROS: reactive oxygen species; TOOKAD: brand name for WST11 or padeliporfin di-potassium; TUNEL: terminal deoxynucleotidyl transferase (TdT)-mediated dUTP nick-end labeling; VCaP: a cell-based model system of human prostate cancer; VTP: vascular targeted photodynamic therapy; WST11: the water-soluble Bchl-D Palladium $3^1$-oxo-15-methoxycarbonylmethyl-rhodobacteriochlorin $13^1$-(2-sulfoethyl) amide dipotassium salt.

BACKGROUND

Prostate cancer represents the most common cause of cancer-related deaths in men, particularly of age 50 or more. Prostate cancer usually develops slowly, so signs may not be seen for many years. The symptoms often only become apparent when the prostate is large enough to affect the urethra, but these symptoms can also be caused by benign prostatic hyperplasia (BPH), a non-cancerous growth of the prostate.

Survival for men with prostate cancer directly depends on the stage and grade of the disease at the time of diagnosis, which is performed by measuring the level of serum prostate-specific antigen (PSA) and conducting a digital rectal examination. The risk of prostate cancer is categorized as low, intermediate and high, based on clinical stage, serum PSA level and Gleason score.

After prostate cancer diagnosis, staging provides important information about the extent of cancer in the body. This is done by measuring the extent of the primary tumor, checking whether the cancer has spread to nearby lymph nodes and/or metastasized to other parts of the body, determining the PSA level at the time of diagnosis and determining the Grade group (based on the Gleason score), which is a measure of how likely the cancer is to grow and spread quickly, as determined by the results of the prostate biopsy (or surgery).

Based on the diagnosis and staging determination, an anticipated response to treatment may be reached. Current treatment choices for prostate cancer include watchful waiting or active surveillance, surgery, radiation therapy, cryotherapy, hormone therapy, chemotherapy, vaccine treatment and bone-directed treatment.

For small, slow-growing cancers localized just in the prostate, watchful waiting or active surveillance without specific therapy is an option, particularly at the very low grade and risk. Only when during active surveillance it is noted that the cancer progressed to intermediate (grade 2) or high (grade 3) risk (for example, involving >3 Gleason score foci) and therefore is a more serious form of cancer, or the cancer is likely to have spread outside the prostate (based on magnetic resonance imaging (MRI) and MRI targeted biopsy)), active treatment is started by radical therapies such as surgery, radiation therapy, cryotherapy, hormone therapy, or chemotherapy.

Hormone therapy, also called androgen deprivation therapy (ADT) or androgen suppression therapy, has the goal to reduce levels of male hormones, called androgens, in the body, or to stop them from stimulating prostate cancer cells to grow. The main androgens in the body are testosterone and dihydrotestosterone (DHT). Most of the androgens are made by the testicles, but the adrenal glands also make a small amount. Lowering androgen levels or stopping them from getting into prostate cancer cells often makes prostate cancers shrink or grow more slowly for a time, but hormone therapy alone does not cure prostate cancer.

Radical therapies of prostate cancer may be unnecessarily aggressive and are associated with important side effects and a risk of overtreatment. Therefore, there has been interest in developing focal therapies that are less aggressive than radical therapies as an alternative treatment option for patients with low-risk prostate cancer [Cathelineaux and Sanchas-Salas, 2016].

Photodynamic therapy (PDT) in general and vascular-targeted PDT (VTP) in particular using novel bacteriochlorophyll derivatives were shown to selectively ablate localized solid tumors in different targets (WO 00/33833; WO 2004/045492) and are suitable for minimally-invasive ablative treatments for prostate cancer.

Vascular targeted photodynamic therapy (VTP) using padeliporfin as a photosensitizer (TOOKAD® Soluble, WST11, padeliporfin) in association with a low power near-infrared laser light in the presence of oxygen destroys targeted tissues. The photosensitizer absorbs light and transfers energy to oxygen molecules creating reactive oxygen species (ROS) such as super oxide and hydroxyl radicals. As WST11 is retained in the tumor vasculature until clearance, generation of intravascular ROS initially induces local vascular destruction resulting in tumor cell necrosis. Padeliporfin is intravenously infused and circulates systemically while only the cancerous lobe of the prostate is illuminated by trans-perineal optic fibers. To treat localized prostate cancer, these probes can be positioned to deliver PDT or VTP to either a portion of, or to the entire, prostate gland. VTP induces irreversible damage to endothelial cells which is quickly followed by a cascade of events including thrombosis, blood stasis and vessel occlusion, leading to tumor necrosis [Ashur et al., 2009; Brandis et al., 2005; Borle et al., 2003].

Positive outcomes from patients with low-risk, localized PCa (Gleason pattern 3 with no previous treatment) treated with WST11/VTP have recently been reported in European multi-center phase 2 and 3 studies. In follow up biopsies at 6 months after prostate hemiablation, 80.6% of the patients were negative for cancer [Azzouzi et al., 2015] and there was a decreased disease progression at 24 months when compared to active surveillance (28% versus 58% respectively, HR 0.34, 95% CI 0.24-0.46; p<0.0001) [Azzouzi et al., 2017]. After a median follow-up of 68 months, 82% of patients treated with WST11/VTP were free of clinically significant cancer in the treated lobes and 76% of the treated patients had avoided a need for subsequent radical therapy [Lebdai et al., 2017]. Thus, after successful clinical trials (Azzouzi et al., 2015, 2017), TOOKAD/padeliporfin/WST11 has been recently approved for use in early stage prostate cancer treatment.

It would be very desirable to improve the efficacy of VTP with a complementary, targeted combination therapy. Furthermore, combination therapy may allow for the extension of VTP treatment to additional cohorts of patients with intermediate or high-risk localized prostate cancer.

SUMMARY OF THE INVENTION

The present invention relates to a method for treatment of prostate cancer or benign prostate hyperplasia by combination therapy comprising administering to a patient in need thereof: (i) a therapeutically effective amount of an androgen-deprivation therapy (ADT) agent (hereinafter "ADT agent"); and (ii) a therapeutically effective amount of a bacteriochlorophyll derivative (herein after "Bchl-D") followed by photodynamic therapy (PDT) or vascular-targeted photodynamic therapy (VTP).

BRIEF DESCRIPTION OF THE DRAWINGS

The patent or application file contains at least one drawing executed in color. Copies of this patent or patent application publication with color drawings will be provided by the United States Patent and Trademark Office upon request and payment of the necessary fee.

FIG. 1A: Top ranked GSEA pathways among the gene sets HALLMARK (left) and Canonical Pathways (C2) (right). FIG. 1B: Enrichment plots from the GSEA with normalized enrichment scores (NES) for androgen response pathways within both gene sets at 6 hr post-VTP (n=4) vs. control (n=4).

FIG. 3A: Degarelix and WST11 VTP combination on tumor growth in athymic nude mice. Mice bearing LNCaP-AR tumors were randomly assigned to 4 cohorts: control (n=7), degarelix (n=9), VTP (n=8), and degarelix+VTP (n=9) and tumor size was measured weekly. The combination treatment suppressed tumor growth more efficiently (p<0.01 for combination vs degarelix, p<0.005 for combination vs VTP). FIG. 3B: Combination of degarelix and VTP on tumor growth in SCID mice. Mice bearing LNCaP-AR tumors were randomly assigned to 4 cohorts: control (n=14), degarelix (n=14), VTP (n=17) and degarelix+VTP (n=16) and tumor size was measured weekly (p<0.0001, combination vs degarelix or VTP). Results were combined from two separate experiments. One dose of degarelix was given at 3 days prior to VTP.

FIG. 5A: Fold changes of serum tPSA were shown at days 1, 3, and 7 post-VTP. Decrease in PSA level was statistically significant in the mice treated with degarelix/VTP on all three days (*p<0.05, ANOVA one way, non-parametric). FIG. 5B: Histological assessment of degarelix and VTP effects on day 7 post-VTP by H&E, AR and TUNEL. Magnifications of 4× and 20× are shown. FIG. 5C: ADT reduces tumor proliferation measured by Ki67. Histological assessment of degarelix effects on day 7 post-VTP by hematoxylin/eosin and Ki67. The number of Ki67 positive cells were reduced in degarelix treated tumors compared to control tumors (p<0.05). Magnifications of 4× and 20× are shown. VTP and combination groups did not retain sufficient viable tumor tissue to quantitatively assess Ki67 staining.

FIG. 6A: A representative H&E and CD31 IHC staining in control and degarelix-treated tumors, with image analysis showing positive pixels in red (lower panels). FIG. 6B: The quantification of CD31 positive areas in the control group (n=12) and the degarelix-treated group (n=11) are shown. Degarelix treatment resulted in a 38% decrease in CD31 staining area compared to controls (P<0.05). Image analysis was performed using QuPath software.

DETAILED DESCRIPTION OF THE INVENTION

Figure 1A:
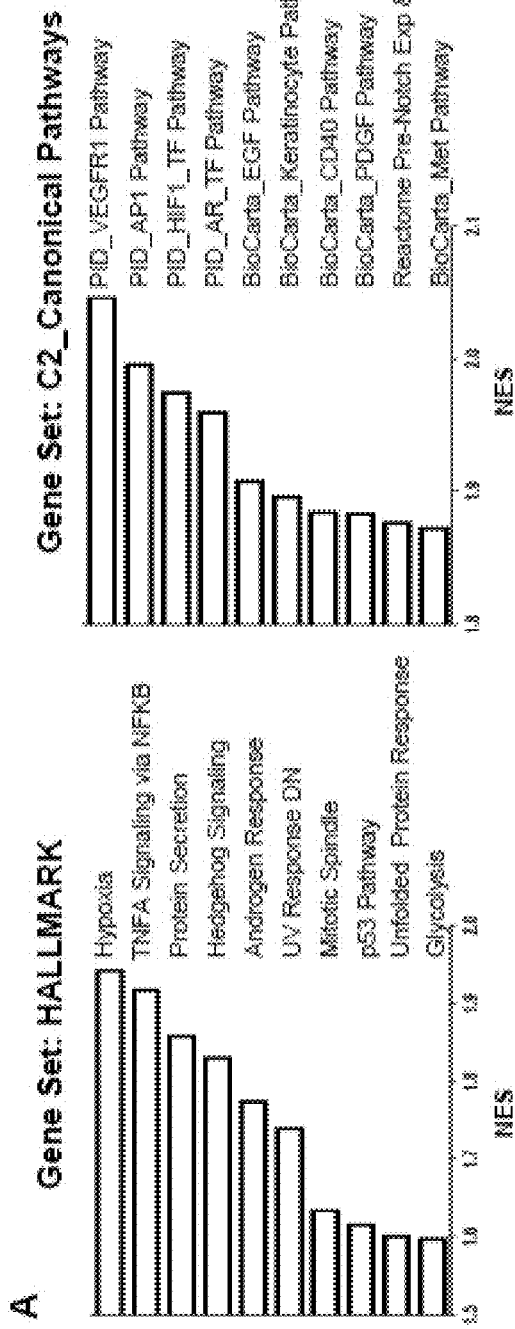
FIGS. 1A-1B depict the transcriptome analysis of LNCaP-AR human prostate cancer xenografts post-VTP treatment with WST11.

While looking for potential druggable pathways active in prostate cancer tumors exposed to VTP, the inventors identified by transcriptome analysis a compensatory, acute upregulation of AR pathway activation following VTP treatment, indicating that inhibition of AR activity by androgen deprivation therapy (ADT) could enhance the efficacy of VTP treatment in prostate cancer.

In certain embodiments, the present invention thus relates to a method for treatment of prostate cancer or benign prostate hyperplasia by combination therapy comprising administering to a patient in need thereof: (i) a therapeutically effective amount of an androgen-deprivation therapy (ADT) agent (hereinafter "ADT agent"); and (ii) a therapeutically effective amount of a bacteriochlorophyll derivative (Bchl-D) followed by photodynamic therapy (PDT) or vascular-targeted photodynamic therapy (VTP) (hereinafter "Bchl-D VTP").

In certain embodiments, the combination therapy provides an enhanced therapeutic effect in the patient compared to the effect of the ADT agent or the Bchl-D followed by PDT or VTP, when each is administered alone.

In certain embodiments, the combination therapy of the ADT agent and the Bchl-D has a synergistic therapeutic effect.

In certain embodiments of the combination therapy, the ADT agent and the Bchl-D agent are administered sequentially.

The ADT agent for use according to the method of the invention may be a chemical castration agent or an antiandrogen agent.

In certain embodiments, the ADT agent is a chemical castration agent. These agents are luteinizing hormonereleasing hormone (LHRH, also called gonadotropin-releasing hormone or GnRH) agonists or antagonists and include drugs such as leuprolide, goserelin, triptorelin, histrelin, and degarelix.

In certain embodiments, the ADT agent is degarelix, a long-acting, gonadotropin-releasing hormone antagonist that results in a rapid onset of medical castration [Broqua et al., 2002; Klotz et al., 2008]. It is useful for treatment of castration-sensitive prostate cancer, including castration-sensitive metastaticprostate cancer.

In certain embodiments, the ADT agent is an antiandrogen agent. These agents include androgen antagonists or testosterone blockers. In certain embodiments, the antiandrogen agent is an androgen receptor (AR) antagonist that binds directly to, and blocks, the AR.

The AR antagonist may be a steroidal antiandrogen drug like cyproterone acetate, megestrol acetate, chlormadinone acetate, medroxyprogesterone acetate, spironolactone, and oxendolone, or a non-steroidal antiandrogen drug like flutamide, bicalutamide, nilutamide, topilutamide, enzalutamide, apalutamide and darolutamide.

In certain embodiments, the ADT agent is enzalutamide, a potent second-generation androgen receptor antagonist approved for the treatment of men with castrate-resistant prostate cancer (CRPC).

Any Bchl-D shown to cause ablation of tumors may be used according to the invention.

In certain embodiments, the Bchl-D for use according to the present invention is a water-soluble anionic bacteriochlorophyll derivative such as those disclosed in the patent publications WO 2004/045492, U.S. Pat. Nos. 7,947,672, and 8,461,142, each and all of which are incorporated by reference herein in its entirety as if fully disclosed therein.

In certain embodiments, the Bchl-D for use according to the present invention is a water-soluble anionic bacteriochlorophyll derivative conjugated with an RGD-containing peptide or RGD-peptidomimetic residue such as those disclosed in the patent publications WO 2008/023378, US 2,012/0294801, WO 2009/107139, U.S. Pat. No. 8,815,213, WO 2010/046900 and U.S. Pat. No. 8,673,270, each and all of which are incorporated by reference herein in its entirety as if fully disclosed therein.

In certain embodiments, the Bchl-D is an anionic Bchl-D of the formula I:

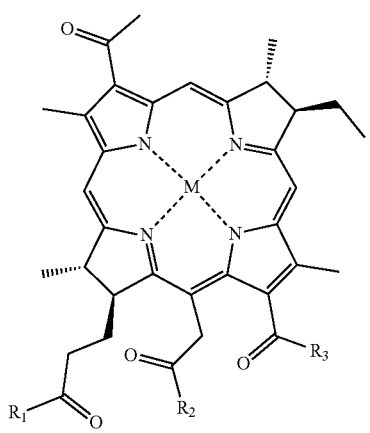

(I)

wherein
M represents 2H or Pd;
$R_1$ is O—$R_4$ or —$NHR_5$, wherein $R_4$ is selected from the group consisting of H, $H^+$, an ammonium group or a monovalent metal cation, and $R_5$ is an RGD-containing peptide or RGD peptidomimetic residue;
$R_2$ is O—$C_1$-$C_6$ alkyl;
$R_3$ is —NH—$(CH_2)_n$—$SO_3^-R_6^-$, wherein n is 2 or 3, and $R_6^+$ is a monovalent metal cation and pharmaceutically acceptable salts and optical isomers thereof.

In certain embodiments, the monovalent metal cation represented by $R_4$ or by $R_{6'}$ is $Na^+$ or $K^+$. In certain embodiments, $R_2$ is methoxy.

In certain embodiments, the anionic Bchl-D for use in the invention has the formula I wherein $R_1$ at position $17^3$ is $OR_4$, namely, the Bchl-D is not conjugated to an RGD-containing peptide or RGD peptidomimetic residue ("non-conjugated Bchl-D"). In certain embodiments, the Bchl-D has the formula I wherein $R_1$ is O—$R_4$, $R_2$ is methoxy, $R_3$ is —NH—$(CH_2)_n$–$SO_3^-$ $R_6^+$, wherein n is 2, $R_4$ and $R_{6'}$ are $K^-$, and M is Pd, as represented by the compound Palladium $3^1$-oxo-15-methoxycarbonylmethyl-rhodobacteriochlorin $13^1$-(2-sulfoethyl) amide dipotassium salt (herein designated WST11). In certain embodiments, the Bchl-D has the formula I wherein $R_1$ is O—$R_4$, $R_2$ is methoxy, $R_3$ is —NH—$(CH_2)_n$–$SO_3^-$ $R_6^+$, wherein n is 2, $R_4$ and $R_{6'}$ are $K^+$, and M is 2H, as represented by the compound $3^1$-oxo-15-methoxycarbonylmethyl-rhodobacteriochlorin $13^1$-(2-sulfoethyl) amide dipotassium salt (herein designated STL-7012). Both Bchl-Ds are disclosed in WO 2004/045492, in which the main inventor is Prof. Avigdor Scherz, a co-inventor in the present application. In certain embodiments, the non-conjugated Bchl-D, e.g., WST11, is intravenously infused to the patient and circulates systemically with no extravasation out of the circulation, namely, it is retained in the tumor vasculature, until clearance. Illumination confined to the cancerous lobe of the prostate using transperineal optic fibers induces ultrafast electron transfer to oxygen molecules in the circulation. The resulting short lived super oxide and hydroxyl radicals initiate rapid destruction of the targeted vasculature followed by a cascade of biological events that end with coagulative necrosis of the tumor. This is vascular-targeted PDT (VTP), a local ablation approach relying upon rapid, free radical-mediated destruction of tumor vasculature. For this reason, in case of VTP, the area to be treated has to be locally illuminated immediately, or at a time of up to 30 min, after the administration of the non-conjugated Bchl-D.

Other non-conjugated anionic Bchl-Ds that can be used according to the invention include the following compounds disclosed in WO 2004/045492: Palladium $3^1$-oxo-15-methoxycarbonylmethyl-rhodobacteriochlorin $13^1$-sulfopropyl) amide dipotassium salt; $3^1$-oxo-15-methoxycarbonylmethyl-rhodobacteriochlorin $13^1$-(2-sulfoethyl) amide dipotassium salt; $3^1$-oxo-15-methoxycarbonylmethyl-rhodobacteriochlorin $13^1$-(3-sulfopropyl) amide dipotassium salt; and Palladium $3^1$-oxo-15-methoxycarbonylmethyl-rhodobacteriochlorin $13^1$-(2-sulfoethyl) amide potassium salt.

In certain embodiments, the Bchl-D for use in the invention is a Bchl-D formula I conjugated to an RGD-containing peptide or RGD peptidomimetic residue (hereinafter "conjugated Bchl-D"). These conjugated Bchl-Ds have the formula I wherein $R_1$ at position $17^3$ is NH—$R_5$, wherein $R_5$ is a non-cyclic or cyclic RGD-containing peptide or RGD peptidomimetic residue.

In certain preferred embodiments, the conjugated Bchl-D for use in the invention is conjugated to a cyclic RGD-containing peptide or to a cyclic RGD peptidomimetic residue. Examples of Bchl-Ds conjugated with cyclic RGD-containing peptide or cyclic RGD peptidomimetic residues for use in the present invention include, but are not limited to, those disclosed in the publications WO 2008/023378 and WO 2010/046900.

In certain embodiments, the conjugated Bchl-D is the $3^1$-oxo-15-methoxycarbonylmethyl-Rhodobacteriochlorin $13^1$-(2-sulfoethyl)amide-$17^3$-(cycloRGDfK) amide potassium salt (herein designated STL-6014), wherein f indicates D-Phe, disclosed in WO 2008/023378.

Other conjugated Bchl-Ds disclosed in WO 2008/023378 that can be used according to the invention include, but are not limited to:

Palladium $3^1$-oxo-15-methoxycarbonylmethyl-Rhodobacteriochlorin $13^1$-(2-sulfoethyl)amide-$17^3$-(cycloRGDfK) amide potassium salt Palladium $3^1$-oxo-15-methoxycarbonylmethyl-Rhodobacteriochlorin $13^1$-(2-sulfoethyl)amide-$17^3$-(cycloRADfK) amide potassium salt Palladium $3^1$-oxo-15-methoxycarbonylmethyl-Rhodobacteriochlorin $13^1$-(2-sulfoethyl)amide-$17^3$-(cycloRGDf-N(Me)K)amide potassium salt When a conjugated Bchl-D, e.g., STL-6014, is administered to the patient, it goes to, and accumulates in, the tumor tissue. Then, upon local illumination, photodynamic generation of ROS is initiated by illuminating the tumor volume and close vicinity once the conjugated Bchl-D accumulates at sufficiently high concentrations and cleared from the surrounding tissue. This is tissue-targeted PDT and an area of the local for treatment is illuminated after some time, to allow accumulation and optimal concentration of the conjugated Bchl-D in the targeted tissue. This time may be of at least 4 h, preferably 6 h, after the administration of the conjugated Bchl-D is completed.

In certain embodiments, the patient's prostate cancer is a low risk prostate cancer. In certain embodiments, the patient's prostate cancer is an intermediate risk prostate cancer. In certain other embodiments, the patient's prostate cancer is a high risk prostate cancer. In certain other embodiments, the patient's prostate cancer is castration-sensitive.

The ADT agent and the Bchl-D may be administered sequentially according to several different regimens. In general, in a session of treatment for ablation of a primary tumor, the PDT or VTP treatment comprises a sole administration of the Bchl-D followed by illumination of an area of the local to be treated, and the ADT treatment comprises several administrations of the ADT agent at various determined time intervals. If necessary, the session may be repeated one or more times as needed.

In accordance with one regimen scheme, the ADT agent is administered once before the sole administration of the Bchl-D followed by PDT or VTP treatment.

In certain embodiments, the present invention provides a method of treating prostate cancer, said method comprising administering to a patient in need thereof: (i) a therapeutically effective amount of an ADT agent; and (ii) a therapeutically effective amount of a bacteriochlorophyll derivative (Bchl-D) followed by PDT or VTP, to provide a combination therapy having an enhanced therapeutic effect compared to the effect of the ADT agent or the Bchl-D PDT or VTP, each administered alone.

The terms "treating" and "treatment" or the phrase "to treat" as used herein refers to any type of treatment that imparts a benefit to a patient afflicted with prostate cancer or benign prostate hyperplasia, including improvement in the condition of the patient (e.g., in one or more symptoms), delay in the progression of the condition, prolongation of survival time, etc.

The term "therapeutically effective amount" as used herein for the ADT agent refers to an amount that is therapeutically effective in the treatment of cancer as defined hereinabove when used in the combination therapy and administered as a single dose or in repeated doses according to the invention. The term "therapeutically effective amount" as used herein for the Bchl-D refers to its capability of causing ablation of the tumor after performance of the PDT or VTP.

The studies described herein and in the figures show that the suggested combination of the two treatment modalities synergizes their impact, leading to primary tumor ablation. These studies and the evolved protocols can be translated into the clinical arena in a straightforward manner.

The invention will now be illustrated by the following non-limitative Examples.

EXAMPLES

Material and Methods (i) Materials: Lyophilized WST11 was obtained from Steba Biotech (Cedex, France). A human prostate cancer cell line VCaP was purchased from ATCC (Manassas, Va.) and LNCaP-AR was kindly provided by Dr. Charles Sawyers (MSKCC). Both cell lines were tested negative for mycoplasma using the MycoAlert™ PLUS Assay from Lonza (Basel, Switzerland). LNCaP-AR cells were cultured in RPMI supplemented with 10% FBS, 2 mmol/L L-glutamine while VCaP cells were cultured in DMEM with high glucose, 10% FBS and 2 mmol/L L-glutamine. All the components for cell culture were from Life Technologies (Grand Island, N.Y.). Degarelix was purchased from Ferring Pharmaceuticals Inc. (Parsippany, N.J.).

(ii) Animal models: All animal work was performed in accordance with a protocol approved by the Institutional Animal Care and Use Committee (IACUC) of Memorial Sloan Kettering Cancer Center. Subcutaneous tumors were established in intact male mice through injection of LNCaP-AR or VCaP human prostate cancer cell lines. LNCaP-AR cells ($2 \times 10^6$) in 100 µL of 1:1 media/Matrigel (BD Biosciences, San Jose, Calif.) were subcutaneously injected into the hindlimb area of 6-8 week old, male, athymic nude mice (NCI, Fredrick, Md.) or SCID mice (C.B-Igh-$1^b$/IcrTac-Prkdc$^{scid}$, Taconic, Hudson, N.Y.). Also VCaP cells ($2 \times 10^6$) were injected into SCID mice (Taconic). Tumor growth was monitored by caliper measurement weekly. When the volume of tumors reached approximately 100 mm³, the animals were randomly assigned to different cohorts for further experiments.

(iii) Treatments:

VTP: An anesthetic cocktail of 150 mg/kg ketamine and 10 mg/kg xylazine was administered intraperitoneally prior to treatment and was supplemented with inhaled isoflurane. A single dose of carprofen (5 mg/kg) and 1 mL of subcutaneous warm saline were administered. WST11 was reconstituted in sterile 5% dextran in water at 2 mg/mL under light protected condition and the aliquots were stored at −20° C. At the day of VTP treatment, an aliquot was thawed and filtered through 0.2 µm disc syringe filter (Sartorius Stedin Biotech North America, Bohemia, N.Y.). The mice were intravenously infused with WST11 via tail vein (9 mg/kg) followed immediately by 10 minutes laser (Ceramoptec, Bonn, Germany) illumination (755 nm, 100 mW/cm for transcriptome analyses and 150 mW/cm for in vivo studies) through a 1 mm frontal fiber (MedLight S. A., Ecublens, Switzerland). The light field was arranged to cover the entire tumor area plus 1 mm rim using red-light aiming beam.

Androgen blockade therapy (ADT): Single dose of degarelix was administered at 0.5 mg per mouse at 3 days before VTP treatment via subcutaneous or intraperitoneal injection. Drug administration was initiated when tumor size reached ~100 mm$^3$.

(iv) PSA detection in serum: Free PSA (inactive PSA) and total PSA (active+inactive PSA) were measured with a dual-label immunofluorometric assay (DELFIA Prostatus™ PSA Free/Total PSA; Perkin-Elmer Life Sciences) according to the manufacturer's recommendations. This assay measures free PSA and complexed PSA in an equimolar fashion [Ulmert et al., 2012; Mitrunen et al., 1995], and the cross-reactivity of PSA-ACT for free PSA is less than 0.2% [Pettersson et al., 1995]. The lower limits of detection are 0.1 ng/mL for both total PSA and free PSA. For detection, the 1235 automatic immunoassay system from Perkin-Elmer Life Sciences (Waltham, Mass.) was used.

(v) Histology and immunohistochemistry: All tumor specimens were fixed in 10% buffered formalin (Fisher Scientific, Pittsburgh, Pa.), processed routinely, embedded in paraffin, sectioned at 5-micron thickness, and stained with hematoxylin-eosin (H&E). Immunohistochemistry (IHC) of tumors was performed on 5 micron formalin-fixed paraffin embedded (FFPE) section following heat induced epitope retrieval (HIER) in a buffer at pH 9.0. AR staining with anti-AR antibody (at 0.66 µg/ml, Abcam, Cambridge, Mass.) and TUNEL staining for cell death with terminal deoxynucleotidyl transferase dUTP nick-end labeling (Roche Diagnostics, Indianapolis, Ind.) was performed using Discovery XT processor (Ventana Medical Systems, Inc., Tucson, Ariz.) at the Molecular Cytology core facility. IHC staining for CD31 and Ki67 markers was performed on FFPE sections at the Laboratory of Comparative Pathology on a Leica Bond RX automated stainer (Leica Biosystems, Buffalo Grove, Ill.). Following HIER at pH 9.0, the primary antibody against CD31 (DIA-310, Dianova, Hamburg, Germany) or Ki67 (ab16667, Abcam, Cambridge, Mass.) was applied at a concentration of 1:250 and 1:100, respectively, followed by application of a polymer detection system (DS9800, Novocastra Bond Polymer Refine Detection, Leica Biosystems). For all IHC stains and TUNEL, the chromogen was 3,3-diaminobenzidine tetrachloride (DAB), and sections were counterstained with haematoxylin. For quantification of CD31, Ki67 and TUNEL staining, whole slide digital images were generated on a scanner (Pannoramic 250 Flash III, 3DHistech, 20×/0.8NA objective, Budapest, Hungary) at a resolution of 0.2431 µm per pixel. Staining quantification was performed with QuPath 0.1.2 software (Centre for Cancer Research & Cell Biology, Queen's University Belfast, UK). For CD31 and Ki67, the region of interest (ROI) was defined as viable tumor tissue excluding necrosis. For TUNEL, the ROI was defined as total tumor tissue including necrosis. For CD31 and TUNEL, the positive area, defined as the ratio of DAB stained pixels to total ROI area, was measured using the positive pixel count algorithm. For Ki67, the ratio (percentage) of cells with positive nuclear staining to total cell number was measured with the positive cell detection algorithm. ROI selection, algorithm optimization and validation, and qualitative examination of H&E slides, were performed by a board-certified veterinary pathologist (SM).

(vi) GSEA for transcriptome analysis of LNCaP-AR xenografts following VTP treatment: LNCaP/AR xenografts were established in intact SCID mice by injecting 2 million cells as described previously [Chen et al., 2004] and, once established, were treated with VTP at 9 mg/kg WST11 followed by 753 nm illumination at 100 mW/cm$^2$ laser fluence. Tumors were collected at 3, 6, or 24 hours, 1 week and 8.5 weeks post VTP and RNA was isolated following the standard protocol using TRIzol (Fisher Scientific). Expression profiling was performed using Illumina HT-12 Expression BeadChip array and the data was analyzed using Partek Genomics Suite (Partek Inc., St. Louis, Mo.). The microarray data then underwent secondary analysis by GSEA [Subramanian et al., 2005] using gene sets from the Hallmark and C2, Canonical Pathways collections (Molecular Signature Databases v6.0 (MSigDB); Broad Institute at http site //software.broadinstitute.org/gsea/msigdb.GSEA| MSigDB. Accessed 19 Jun. 2017. Microarray data has been deposited in the National Center for Biotechnology Information Gene Expression Omnibus (GEO) (GSE109681).

(vii) Statistical analysis: Two-way ANOVA test using GraphPad Prism (GraphPad Software, La Jolla, Calif.) was used for therapeutic efficacy in affecting tumor growth, and One-way ANOVA for PSA and a Mann-Whitney test for CD31, Ki67 or TUNEL staining quantification. Differences with p values<0.05 were considered statistically significant.

EXAMPLES

Example 1

Figure 1B:
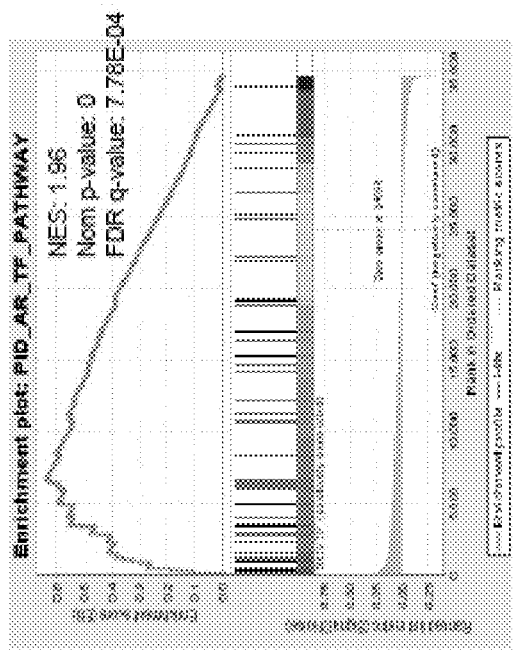
Figure 1B:
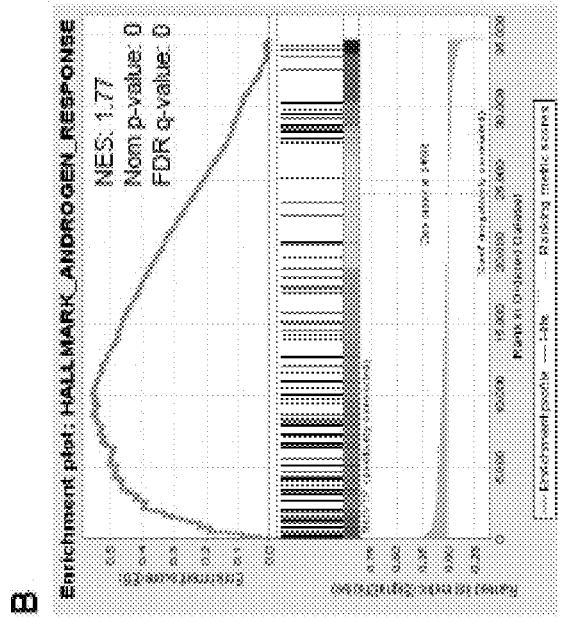

Transcriptome Analysis of WST11 VTP-Treated Tumors by GSEA Revealed an Enrichment of Androgen Response Pathways To identify potential druggable pathways active in PCa that could be exploited for combination therapy with VTP, we analyzed the transcriptome of LNCaP-AR xenograft tumors following acute response to VTP exposure. Using the LNCaP-AR prostate cancer model system, we employed microarrays and Gene Set Enrichment Analysis (GSEA) to identify potential druggable pathways active in tumors exposed to VTP. Three to six hours post-VTP, androgen responsive gene sets were enriched, suggesting that the androgen receptor (AR) may be a viable target in combination with VTP. Unbiased GSEA identified statistically significant enrichments with gene sets related to hypoxia, HIF1A, and VEGFR pathways at three to six hours post-VTP treatment (FIGS. 1A-1B), effects that have previously been shown to be associated with photodynamic therapies (PDT) [Broekgaarden et al., 2015]. Interestingly, AR signaling gene sets were also up-regulated in VTP-treated tumors compared to control mice, suggesting that the AR may be a viable target for combination therapy with VTP.

Example 2

ADT and VTP Displays Potential Enhanced Effects: LNCaP-AR Model

Figure 2:
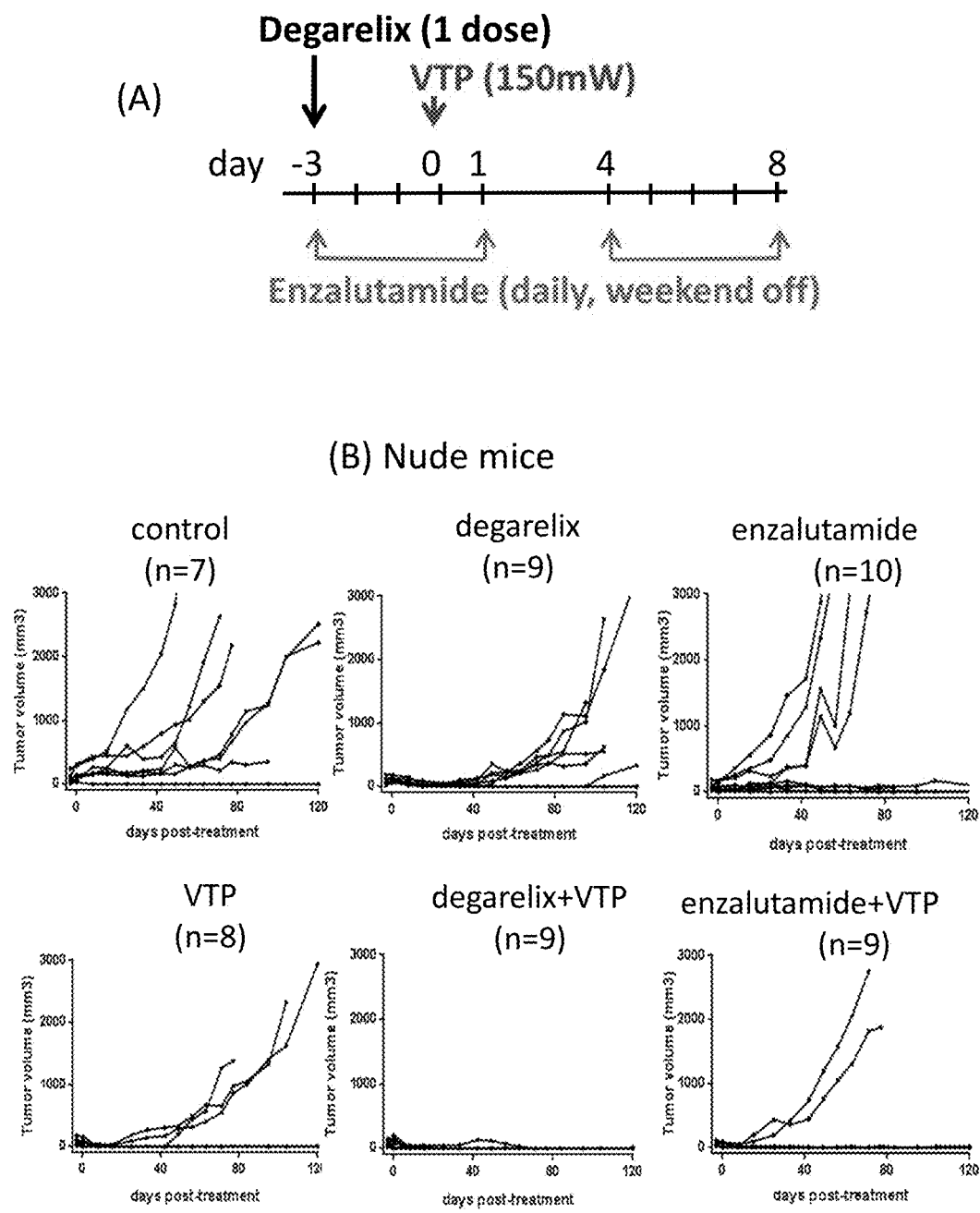
FIG. 2 shows that ADT in combination with WST11/VTP displays potential enhanced effects: LNCaP-AR human prostate cancer model in nude mice. Panel A: Treatment scheme showing administration of a sole dose of degarelix (0.5-1.0 mg per mouse) 3 days prior to VTP, and of enzalutamide (30 mg/kg) daily for two weeks total both before and after VTP. Panel B: Mice bearing LNCaP-AR tumors were randomly assigned to 6 cohorts: control (n=7), degarelix (n=9), enzalutamide (n=10), VTP (n=8), degarelix+VTP (n=9), and enzalutamide+VTP (n=9) and tumor size was measured weekly.

We tested this hypothesis in mice bearing LNCaP-AR xenograft tumors by using the AR pathway inhibitors degarelix (to achieve pharmacological castration) or enzalutamide (AR antagonist), alone or in combination with VTP. Degarelix was administered as a single 0.5-1 mg dose 3 days prior to initiation of VTP, while enzalutamide (30 mg/kg) was given daily for two weeks total both before and after VTP (FIG. 2, Panel A). Nude mice bearing LNCaP-AR tumors were randomly assigned to 6 cohorts: control (n=7), degarelix (n=9), enzalutamide (n=10), VTP (n=8), degarelix+VTP (n=9), and enzalutamide+VTP (n=9) and tumor size was measured weekly. The results in FIG. 2, Panel B show that compared to either AR pathway inhibitor or VTP used alone, degarelix or enzalutamide in combination with VTP significantly inhibited tumor growth.

Example 3

Figure 3A:
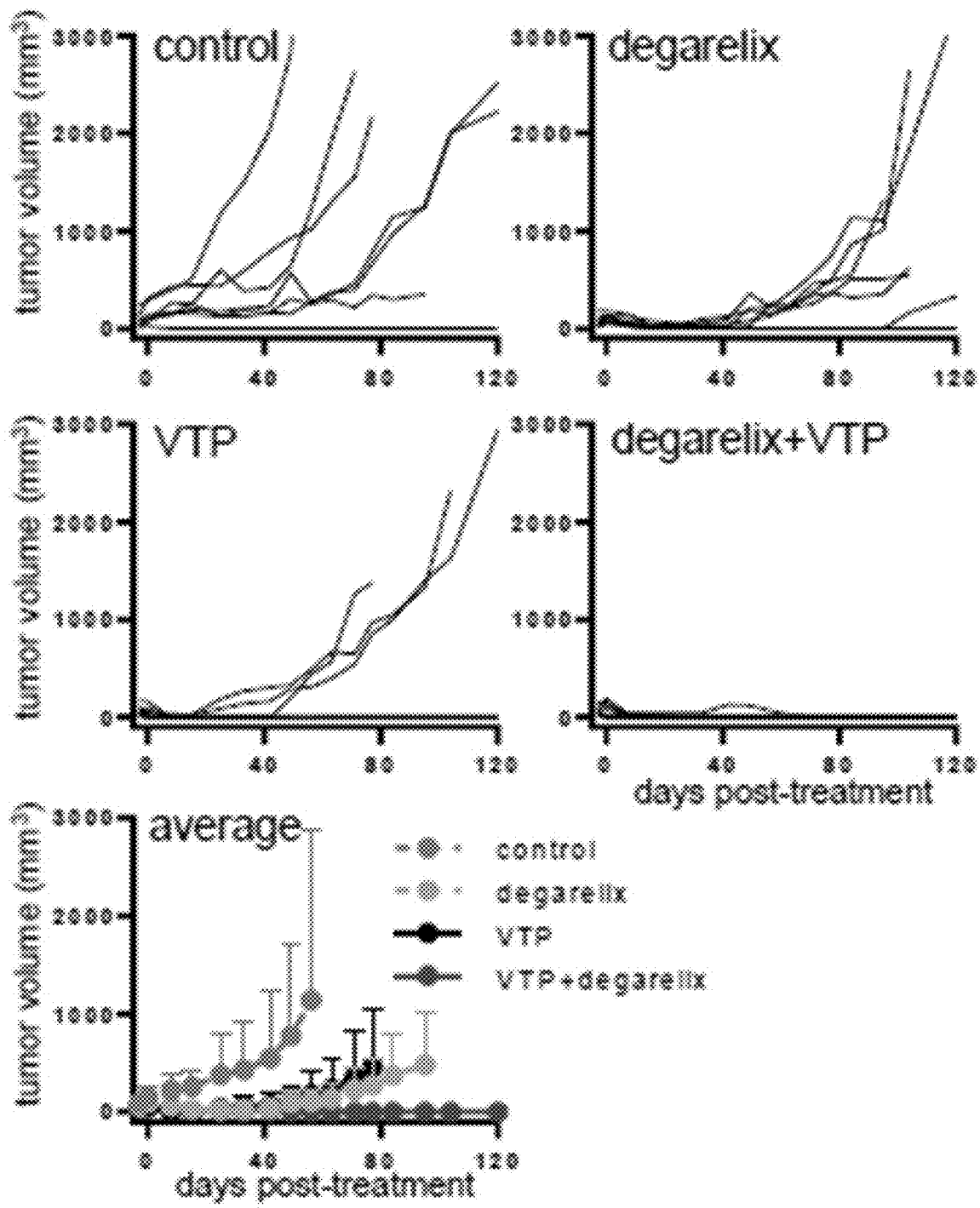
FIGS. 3A-3B show the efficacy of the ADT and WST11/VTP combination in the LNCaP-AR human prostate cancer model in nude and SCID mice.
Figure 3B:
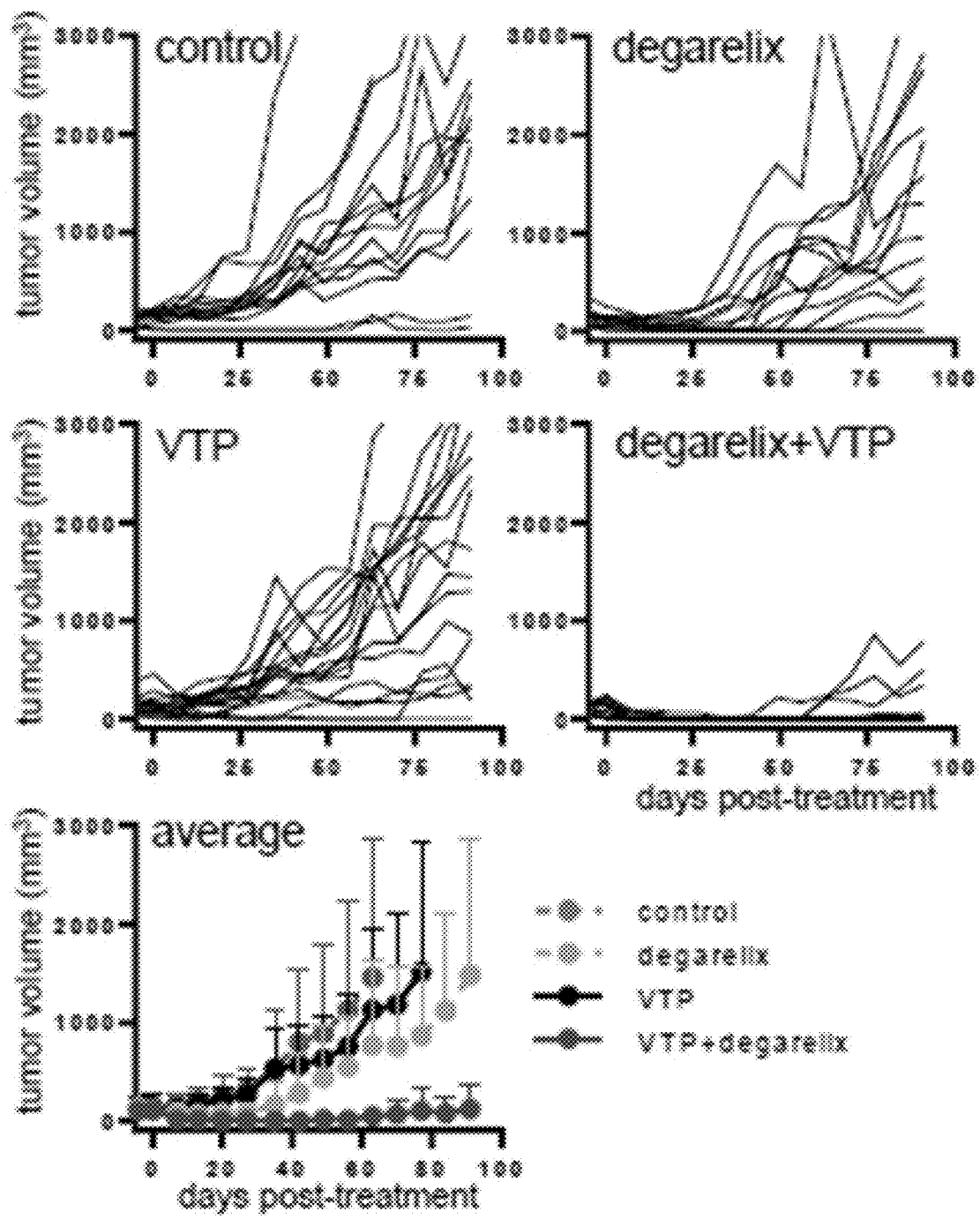

Combination Therapy of ADT with WST11/VTP Suppressed Tumor Growth to a Greater Extent than Either Treatment Alone in a LNCaP-AR Human Prostate Cancer Model in Nude Mice and SCID Mice To test our hypothesis that the preemptive blocking of androgen signaling upregulation induced by VTP might improve the outcome of tumor growth control, we tested combination of VTP with an androgen signaling pathway inhibitor in widespread clinical use for the treatment of PCa. To establish preexisting AR inhibition, treatment with degarelix was initiated three days prior to administering VTP to PCa xenograft tumors. Prior studies with WST11 VTP established that components of the immune response contributed to the anticancer activity of VTP [Preise et al., 2009]. Therefore, the efficacy of the combination therapy was compared against LNCaP-AR tumors in both athymic nude (T cell deficient) (FIG. 3A) and severe combined immunodeficiency (SCID) (both T and B cell deficient) (FIG. 3B) mice. Tumor-bearing nude mice were randomly assigned to four cohorts: control, degarelix, VTP, and degarelix and VTP combination. The combination of degarelix and VTP resulted in statistically significant improved tumor growth control compared to either degarelix ($p<0.01$) or VTP alone ($p<0.005$) (FIG. 3A). As in the nude mouse, the combination of degarelix and VTP led to superior control of LNCaP-AR tumor growth in SCID mice ($p<0.0001$ for either monotherapy vs. combination) (FIG. 3B).

Example 4

Figure 4:
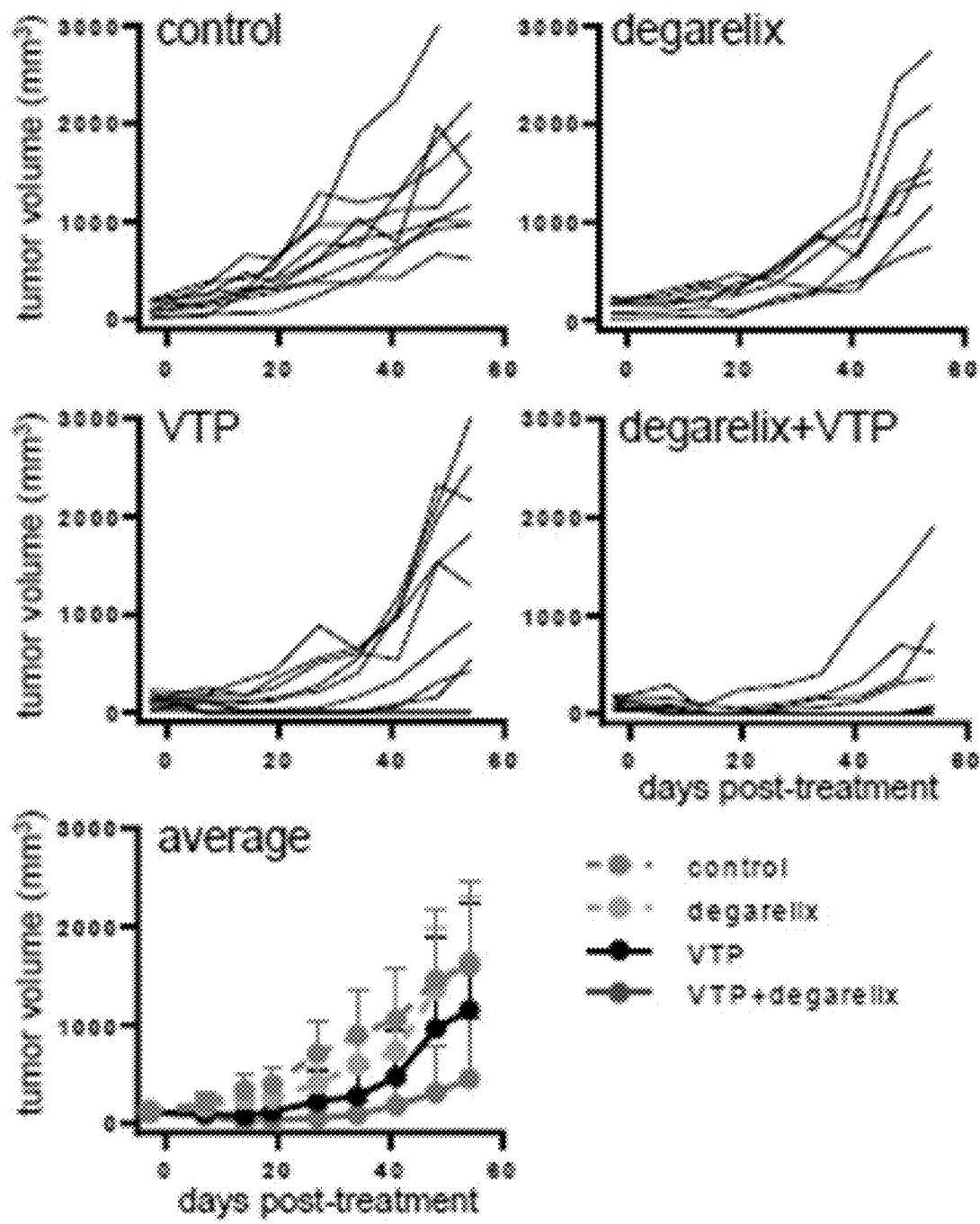
FIG. 4 shows the efficacy of ADT and WST11/VTP combination in the VCaP human prostate cancer model in SCID mice. SCID mice bearing VCaP tumors were randomly assigned to 4 cohorts: control (n=7), degarelix (n=9), VTP (n=8), degarelix+VTP (n=9) and tumor size was measured weekly. One dose of degarelix was given 3 days prior to VTP treatment. Combination therapy led to superior local tumor control compared to monotherapy (p<0.0001 for degarelix, p<0.005 for VTP).

Combination Therapy of ADT with WST11/VTP Delayed Tumor Growth to a Greater Extent than Either Treatment Alone in the VCaP-AR Human Prostate Cancer Model in SCID Mice SCID mice bearing VCaP tumors were randomly assigned to 4 cohorts: control (n=7), degarelix (n=9), VTP (n=8), degarelix+VTP (n=9), and tumor size was measured weekly. One dose of degarelix was given 3 days prior to VTP treatment. The combination of degarelix and VTP was significantly more effective than VTP alone ($p<0.005$) or degarelix alone ($p<0.0001$) (FIG. 4) in delaying the growth of VCaP, a human PCa model with AR gene amplification that also expresses the constitutively active AR splice variant AR-V7.

Example 5

Figures 5A, 5B:
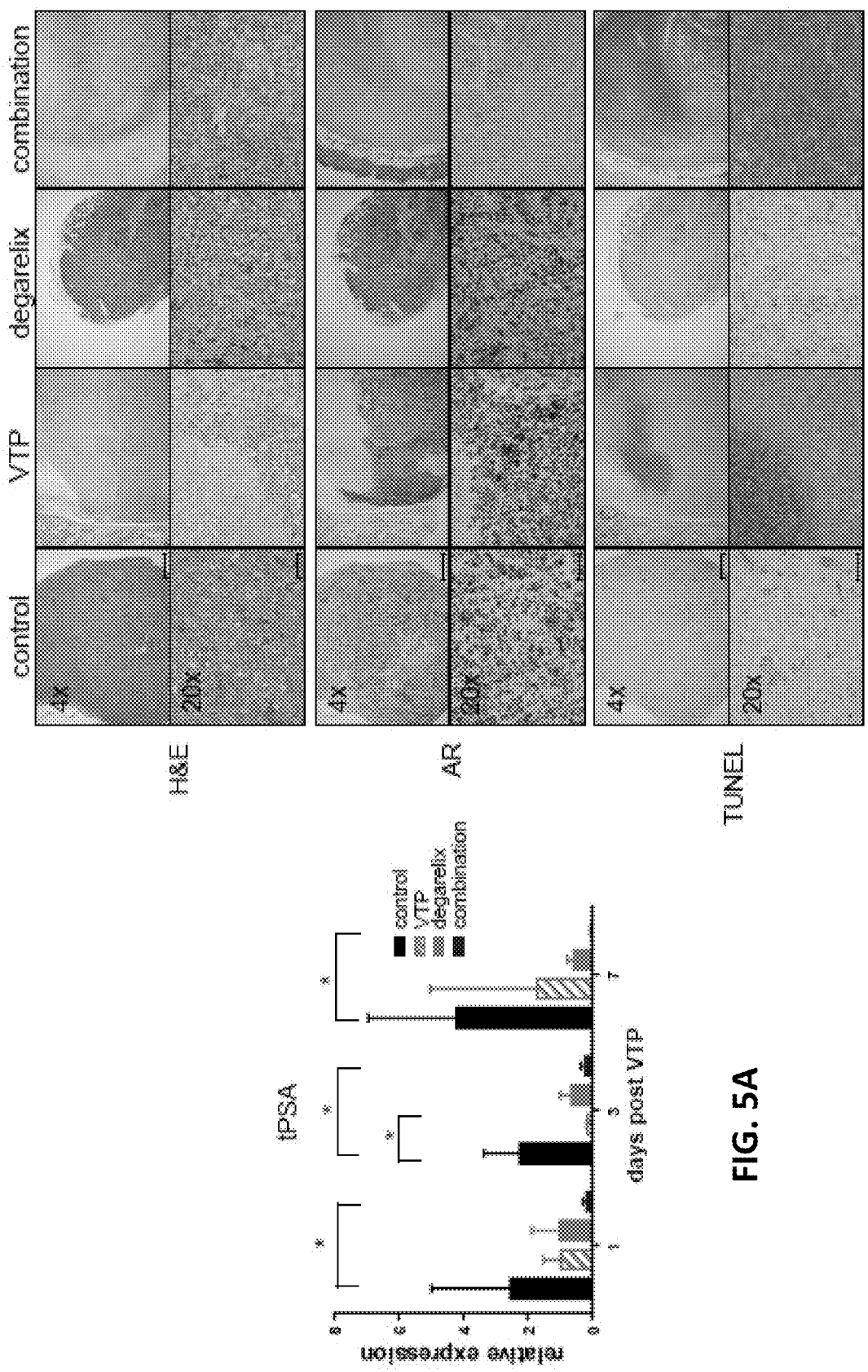
FIGS. 5A-5C show superior local tumor control by ADT and WST11/VTP combination correlated with a decline in serum PSA and intense TUNEL staining, but not in Ki67 staining.

Combination Therapy of ADT and VTP was More Effective than VTP Alone in Downregulation of Total PSA Levels and Induction of Apoptosis/Necrosis To verify that AR activity was inhibited by the treatments, the levels of total PSA (tPSA) in serum of mice bearing LNCaP-AR tumors were measured. Serum tPSA values were determined in separate cohorts of mice at one, three, or seven days post-WST11 VTP (four, six or ten days post-degarelix). As shown in FIG. 5A, fold changes of tPSA values declined by either VTP or degarelix alone, but the sharpest drop in tPSA levels was seen with the combination of degarelix and WST11 VTP ($p<0.05$ vs. control across all time points).

Figure 5C:
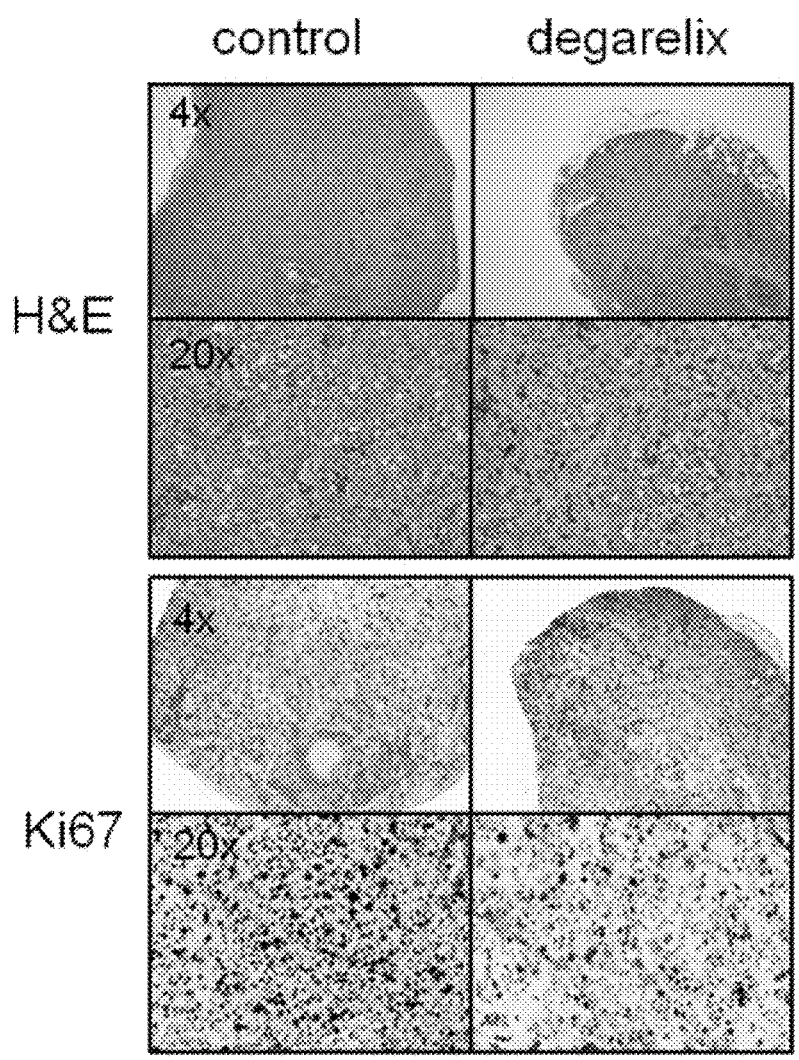

In parallel, the histology of control, VTP, degarelix and degarelix+VTP combination treated tumors on days three and seven post-VTP was assessed by both hematoxylin/eosin (HE) and TUNEL assay to detect cell death (apoptotic and/or necrotic cells). As shown in FIG. 5B, VTP-treated tumors displayed partial cell death characterized by large foci of TUNEL staining, but with significant TUNEL negative areas. Tumors treated with combination therapy appeared to display more extensive areas of TUNEL staining. Although not statistically significant compared to VTP alone, there were fewer tumor cells that escaped death in the combination group, suggesting that increased cell death underlies the effect on tumor inhibition. In contrast, degarelix alone treated tumors exhibited little TUNEL staining, but still showed reduced Ki67 signal compared to controls, as expected ($p<0.05$, FIG. 5C). Nuclear AR staining was inversely correlated with TUNEL, suggesting that viable AR-positive cells had escaped focal therapy effects of WST11 VTP alone. Notably, the tumors treated with combination therapy were absent of AR staining, suggesting that remaining viable tumor cells we few in number.

Example 6

ADT Reduces the Number of Vessels in Tumors

Figure 6A:
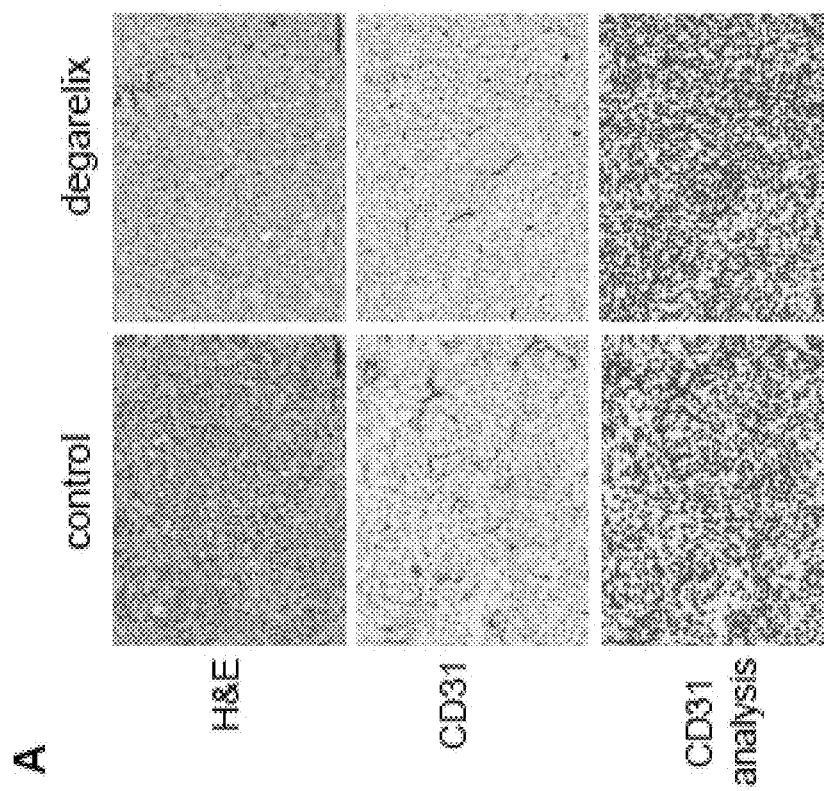
FIGS. 6A-6B show that ADT reduces the number of vessels in tumors.
Figure 6B:
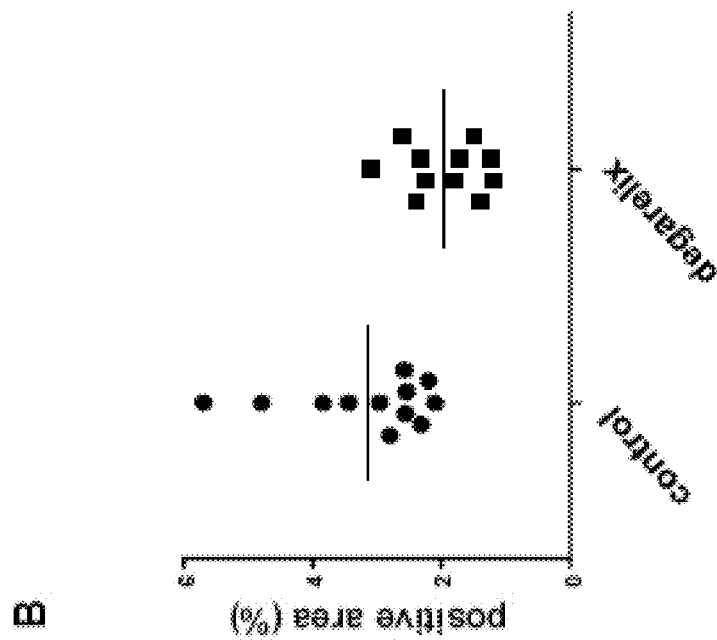

CD31 is primarily a marker for endothelial cells which can help evaluate the degree of intratumoral vessel formation. This is achieved by CD31 H&E and immunohistochemical (IHC) staining of control and degarelix-treated tumors. As shown in FIG. 6A, the image analysis showing positive pixels in red (lower panels) indicates that degarelix-treated tumors (right panel) appear to have fewer vessels than tumors in the control group (left panel). The quantification of CD31 positive areas in the control group (n=12) and the degarelix-treated group (n=11) in FIG. 6B show that degarelix treatment resulted in a 38% decrease in CD31 staining area compared to controls ($p<0.05$).

Discussion

The effective adoption of prostate cancer screening has led to earlier detection of small, clinically significant prostate cancers amenable to the newly developed treatment strategies for partial gland ablation which are well tolerated and associated with fewer adverse side effects than aggressive radical therapies such as surgery and radiation.

Positive oncologic outcomes in clinical studies of VTP has led to the recent approval of TOOKAD® Soluble (WST11 or padeliporfin) for the treatment of low-risk PCa and highlights the potential of VTP to serve as an alternative to active surveillance or radical therapies (Azzouzi et al., 2015; Azzouzi et al., 2017; Lebdai et al., 2017). To potentially extend VTP treatment to larger cohorts of patients, VTP clinical trials are planned for patients with localized PCa of intermediate risk, Grade Group 2 [Gleason score 7 (3+4)].

REFERENCES

Ashur I, Goldschmidt R, Pinkas I, Salomon Y, Szewczyk G, Sarna T, et al. Photocatalytic generation of oxygen radicals by the water-soluble bacteriochlorophyll derivative WST11, noncovalently bound to serum albumin *J Phys Chem A* 2009; 113:8027-37.

Azzouzi A R, Barret E, Bennet J, Moore C, Taneja S, Muir G, et al. TOOKAD® Soluble focal therapy: pooled analysis of three phase II studies assessing the minimally invasive ablation of localized prostate cancer. *World J Urol* 2015; 33:945-53.

Azzouzi A-R, Vincendeau S, Barret E, Cicco A, Kleinclauss F, van der Poel H G, et al. Padeliporfin vascular-targeted photodynamic therapy versus active surveillance in men with low-risk prostate cancer (CLIN1001 PCM301): an open-label, phase 3, randomised controlled trial. *Lancet Oncol* 2017; 13:181-91.

Borle F, Radu A, Fontolliet C, van den Bergh H, Monnier P, Wagnières G. Selectivity of the photosensitiser Tookad for photodynamic therapy evaluated in the Syrian golden hamster cheek pouch tumour model. *Br J Cancer* 2003; 89:2320-26.

Brandis A, Mazor O, Neumark E, Rosenbach-Belkin V, Salomon Y, Scherz A. Novel water-soluble bacteriochlorophyll derivatives for vascular-targeted photodynamic therapy: synthesis, solubility, phototoxicity and the effect of serum proteins. *Photochem Photobiol* 2005; 81:983-93.

Broekgaarden M, Weijer R, van Gulik T M, Hamblin M R, Heger M. Tumor cell survival pathways activated by photodynamic therapy: a molecular basis for pharmacological inhibition strategies. *Cancer Metastasis Rev* 2015; 34:643-90.

Broqua P, Riviere P J-M, Conn P M, Rivier J E, Aubert M L, Junien J-L. Pharmacological profile of a new, potent, and long-acting gonadotropin-releasing hormone antagonist: degarelix. *J Pharmacol Exp Ther* 2002; 301:95-102.

Cathelineau X, Sanchez-Salas R. Focal Therapy for Prostate Cancer: Pending Questions. *Curr Urol Rep* 2016; 17:86.

Chen C D, Welsbie D S, Tran C, Baek S H, Chen R, Vessella R, et al. Molecular determinants of resistance to antiandrogen therapy. *Nat Med* 2004; 10:33-39

Klotz L, Boccon-Gibod L, Shore N D, Andreou C, Persson B-E, Cantor P, et al. The efficacy and safety of degarelix: a 12-month, comparative, randomized, open-label, parallel-group phase III study in patients with prostate cancer. *BJU Int* 2008; 102:1531-8

Lebdai S, Bigot P, Leroux P-A, Berthelot L-P, Maulaz P, Azzouzi A-R. Vascular Targeted Photodynamic Therapy with Padeliporfin for Low Risk Prostate Cancer Treatment: Midterm Oncologic Outcomes. *J Urol* 2017; doi:10.1016/j.juro.2017.03.119.

Mitrunen K, Pettersson K, Piironen T, Björk T, Lilja H, Lövgren T. Dual-label one-step immunoassay for simultaneous measurement of free and total prostate-specific antigen concentrations and ratios in serum. *Clin Chem* 1995; 41:1115-20.

Pettersson K, Piironen T, Seppälä M, Liukkonen L, Christensson A, Matikainen M T, et al. Free and complexed prostate-specific antigen (PSA): in vitro stability, epitope map, and development of immunofluorometric assays for specific and sensitive detection of free PSA and PSA-alpha 1-antichymotrypsin complex. *Clin Chem* 1995; 41:1480-88.

Preise D, Oren R, Glinert I, Kalchenko V, Jung S, Scherz A, et al. Systemic antitumor protection by vascular-targeted photodynamic therapy involves cellular and humoral immunity. *Cancer Immunol Immunother* 2009; 58: 71-84.

Subramanian A, Tamayo P, Mootha V K, Mukherjee S, Ebert B L, Gillette M A, et al. Gene set enrichment analysis: a knowledge-based approach for interpreting genomewide expression profiles. *Proc Natl Acad Sci USA* 2005; 102: 15545-50.

Ulmert D, Evans M J, Holland J P, Rice S L, Wongvipat J, Pettersson K, et al. Imaging androgen receptor signaling with a radiotracer targeting free prostate-specific antigen. *Cancer Discov* 2012; 2:320-27.

What is claimed is:

1. A method for treatment of prostate cancer by combination therapy comprising administering to a patient in need thereof: (i) a therapeutically effective amount of an androgen-deprivation therapy (ADT) agent (hereinafter "ADT agent"); and (ii) a therapeutically effective amount of a bacteriochlorophyll derivative (Bchl-D) followed by vascular-targeted photodynamic therapy (VTP) (hereinafter "Bchl-D VTP"), wherein said ADT agent is degarelix that is administered once or in repeated doses, during several days, before and optionally after administration of said Bchl-D.

2. The method of claim 1, wherein the Bchl-D is an anionic bacteriochlorophyll derivative optionally conjugated with an RGD-containing peptide or RGD-peptidomimetic residue.

3. The method of claim 2, wherein the Bchl-D has the formula I:

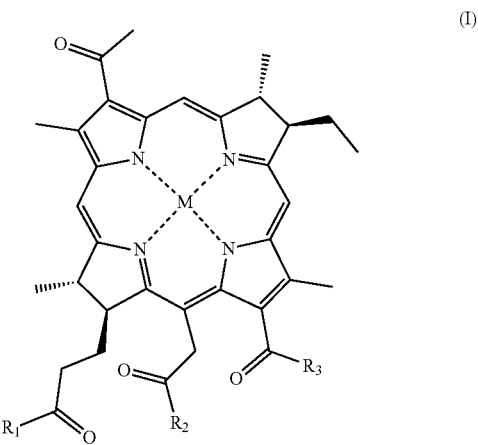

wherein
M represents 2H or Pd;
$R_1$ is O—$R_4$ or —$NHR_5$, wherein $R_4$ is selected from the group consisting of H, $H^+$, an ammonium group or a monovalent metal cation, and $R_5$ is an RGD-containing peptide or RGD peptidomimetic residue;
$R_2$ is —O—$C_1$-$C_6$ alkyl;
$R_3$ is —NH—$(CH_2)_n$—$SO_3^-R_6^-$, wherein n is 2 or 3, and $R_6^+$ is a monovalent metal cation; or
pharmaceutically acceptable salts or optical isomers thereof.

4. The method of claim 3, wherein the monovalent metal cation represented by $R_4$ and $R_6^+$ each or both are $Na^+$ or $K^+$, and $R_2$ is methoxy.

5. The method of claim 4, wherein $R_1$ is O—$R_4$, $R_2$ is methoxy, $R_3$ is —NH—$(CH_2)_n$—$SO_3^-R_6^+$, wherein n is 2, and $R_4$ and $R_6^+$ are K.

6. The method of claim 5, wherein the Bchl-D of formula I is the compound Palladium $3^1$-oxo-15-methoxycarbonylmethyl-rhodobacteriochlorin $13^1$-(2-sulfoethyl) amide dipotassium salt (herein designated WST11) or the compound $3^1$-oxo-15-methoxycarbonylmethyl-rhodobacteriochlorin $13^1$-(2-sulfoethyl) amide dipotassium salt (herein designated STL-7012).

7. The method of claim 6, wherein the area to be treated by said VTP is locally illuminated immediately after the administration of the Bchl-D.

8. The method of claim 6, wherein the area to be treated by said VTP is locally illuminated at a time of up to 30 min after the administration of the Bchl-D.

9. The method of claim 4, wherein in the Bchl-D of formula I $R_1$ is NH—$R_5$, and $R_5$ is a cyclic RGD-containing peptide or a cyclic RGD-peptidomimetic residue.

10. The method of claim 9, wherein the Bchl-D is STL-6014.

11. The method of claim 1, wherein the Bchl-D derivative is WST11.

12. The method of claim 11, wherein the WST11 is administered once and degarelix is administered once before and one or several times after the administration of WST11 at determined time intervals.

13. The method of claim 1, wherein the prostate cancer is a low risk prostate cancer.

14. The method of claim 1, wherein the prostate cancer is an intermediate risk prostate cancer.

15. The method of claim 1, wherein the prostate cancer is a high risk prostate cancer.

16. The method of claim 1, wherein the prostate cancer is castration-sensitive.

17. The method of claim 11, wherein degarelix is administered as a single dose several days before administration of WST11, which is followed by VTP.

18. The method of claim 17, wherein degarelix is administered to the patient as a single dose 3 days before administration of WST11, which is followed by immediate laser local illumination of the area at 755 nm.

* * * * *